US010241010B2

(12) United States Patent
Coleman et al.

(10) Patent No.: US 10,241,010 B2
(45) Date of Patent: Mar. 26, 2019

(54) APPARATUS AND METHODS OF COLLECTING AND SAMPLING HYDROCARBON FLUIDS

(71) Applicant: Weatherford Technology Holdings, LLC, Houston, TX (US)

(72) Inventors: Todd M. Coleman, Fairmount, IL (US); Corben C. Rice, Penfield, IL (US); Dennis D. Coleman, Champaign, IL (US)

(73) Assignee: Weatherford Technology Holdings, LLC, Houston, TX (US)

( * ) Notice: Subject to any disclaimer, the term of this patent is extended or adjusted under 35 U.S.C. 154(b) by 396 days.

(21) Appl. No.: 14/676,577

(22) Filed: Apr. 1, 2015

(65) Prior Publication Data
US 2015/0285716 A1    Oct. 8, 2015

Related U.S. Application Data

(60) Provisional application No. 61/975,579, filed on Apr. 4, 2014.

(51) Int. Cl.
*G01N 1/22*    (2006.01)
*B65D 75/58*    (2006.01)
(Continued)

(52) U.S. Cl.
CPC ............ *G01N 1/2202* (2013.01); *G01N 1/22* (2013.01); *G01N 1/405* (2013.01); *B65D 75/5883* (2013.01); *G01N 31/224* (2013.01)

(58) Field of Classification Search
CPC ........ G01N 1/2202; G01N 1/22; G01N 1/405; G01N 31/224; B65D 75/5883
(Continued)

(56) References Cited

U.S. PATENT DOCUMENTS

| 4,792,526 A | * | 12/1988 | Ouellette | ............... G01V 9/007 436/139 |
| 5,047,073 A | * | 9/1991 | Stetter | .................... B01D 53/30 95/8 |

(Continued)

FOREIGN PATENT DOCUMENTS

JP    2002053138 A    2/2002

OTHER PUBLICATIONS

Australian Examination Report dated Apr. 5, 2017, for Australian Patent Application No. 2015240667.
(Continued)

*Primary Examiner* — Helen C Kwok
*Assistant Examiner* — Nashmiya S Fayyaz
(74) *Attorney, Agent, or Firm* — Patterson & Sheridan, LLP (57) ABSTRACT

Methods and apparatus for the collection, transportation, and analysis of gas samples which may be required in various scientific, environmental, and natural resource contexts is provided. An isolating container for removing a component from a fluid sample includes a body defining a sampling chamber having a first end and a second end; a first valve assembly coupled to the first end; a reactant material positioned within the sampling chamber for reacting with the component; and a second valve assembly coupled to the second end, wherein the fluid sample enters the sampling chamber through the first valve assembly and exits through the second valve assembly.

15 Claims, 9 Drawing Sheets

(51) Int. Cl.
*G01N 1/40* (2006.01)
*G01N 31/22* (2006.01)

(58) Field of Classification Search
USPC ...................................................... 73/864.63
See application file for complete search history.

(56) References Cited

U.S. PATENT DOCUMENTS

| | | | |
|---|---|---|---|
| 5,140,845 | A | 8/1992 | Robbins |
| 6,439,429 | B1 | 8/2002 | Gross |
| 2004/0107782 | A1 | 6/2004 | Bradley et al. |
| 2006/0286606 | A1 | 12/2006 | Oliver |
| 2008/0260587 | A1* | 10/2008 | Coleman ................ G01N 30/88 422/89 |
| 2011/0048107 | A1 | 3/2011 | Schulten et al. |
| 2012/0234114 | A1 | 9/2012 | Coleman et al. |

OTHER PUBLICATIONS

Canadian Office Action dated Jun. 12, 2018, for Canadian Patent Application No. 2,943,867.
PCT International Search Report and Written Opinion dated Sep. 16, 2015, for International Application No. PCT/US2015/024098.

\* cited by examiner

APPARATUS AND METHODS OF COLLECTING AND SAMPLING HYDROCARBON FLUIDS

BACKGROUND OF THE INVENTION

Field of the Invention

Embodiments of the present invention generally relate to containers and methods for the collection, transportation and analysis of fluid samples.

Description of the Related Art

Having the ability to collect, differentiate and categorize different gas mixtures and their individual components has long been a necessity for the purposes of energy exploration and source identification of stray gases (i.e., differentiating gases from landfills, gas storage fields, producing wells, etc.). However, in order to do so successfully, one often needs to obtain samples from different potential source gases, and then submit the samples for detailed testing and comparison. Because analysis of the chemical composition can often be inconclusive in differentiating similar gases, isotope analysis of individual components of the gas can often provide an effective means of distinguishing two otherwise chemically identical gas sources. For instance, methane from a sanitary landfill is isotopically different from methane associated with petroleum. Similarly, isotope analysis of certain gas components can also provide insight to the mechanism of formation of the gases, and therefore give insight into the commercial viability of the gas source. Unfortunately, the transfer and shipment of hazardous materials (e.g., flammable and/or toxic gases) is often costly and usually requires specialized training. In some instances, air shipment of such gases is strictly forbidden (i.e. toxic gases). One such component of interest often associated with natural gas is hydrogen sulfide ($H_2S$).

Typical ways of collecting gases containing hydrogen sulfide ($H_2S$) have included the use of containers like gas bags, chemically treated metal cylinders, and glass vials. Such containers are often fragile, expensive and unwieldy. In some instances, samples containing toxic concentrations of $H_2S$ are strictly forbidden on aircraft. In parts of the world where isotope analysis is not available, the only means of transporting such samples to a laboratory with isotope analysis capability would be via ocean freight, and then via ground transport. This procedure often consumes valuable time and resources, as the shipping of hazardous materials involves specialized training for the shipper as well as associated hazardous shipping fees and restrictions. $H_2S$ is also highly reactive and may react with the vessel in which it is contained. For instance, untreated stainless steel cylinders can completely "remove" $H_2S$ from a gas mixture.

Once in the lab, the current technology for extracting sulfur from $H_2S$ for isotopic analysis is to flow the gas through various solutions. The current solutions include cadmium acetate, silver phosphate, zinc acetate, and silver phosphate/silver nitrate solutions. All of these methods utilize liquid solutions and except for zinc acetate are hazardous.

Therefore, there is a need for improved containers and methods for the collection, transportation, and analysis of fluid samples.

SUMMARY OF THE INVENTION

Embodiments of the present invention generally relate to containers and methods for the collection, transportation and analysis of fluid samples.

In one embodiment, an isolating container for removing a component from a fluid sample includes a body defining a sampling chamber having a first end and a second end; a first valve assembly coupled to the first end; a reactant material positioned within the sampling chamber for reacting with the component; and a second valve assembly coupled to the second end, wherein the fluid sample enters the sampling chamber through the first valve assembly and exits through the second valve assembly.

In another embodiment, a method for collecting a fluid sample includes flowing the fluid sample into an isolating container, wherein the isolating container includes a reactant material; removing a component from the fluid sample by reacting the component with the reactant material; and collecting the fluid sample leaving the isolating container into a sample container.

In another embodiment, a sample container for collecting a fluid sample includes a container body; a flat end portion; and a valve assembly disposed at the flat end portion for accessing the interior of the container body.

In another embodiment, an adapter for coupling a Luer activated valve to an activating device includes a connect body having a bore, a first end for coupling with the Luer activated valve, and a second end for coupling with the activating device; and a pin movably disposed in the bore of the connect body, wherein the pin is movable by the activating device to activate the Luer activated valve.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIGS. 2-1 to 2-11 illustrate an exemplary process of isolating a target component from a fluid sample.

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION

Embodiments of the present invention provide sample containers and methods for the safe and cost efficient collection and transportation of fluid samples. In certain embodiments described herein, the containers and methods provided herein circumvent current hazardous materials regulations by removing hazardous gases (e.g., $H_2S$) from the fluid sample, thereby allowing the fluid sample to be shipped by traditional means (e.g., post, courier service, or air freight). Thus, embodiments of the containers and methods for the collection and transportation of fluid sample eliminate the need for HAZMAT training for the shipper as well as fees associated with the shipment of hazardous materials.

Figure 1:
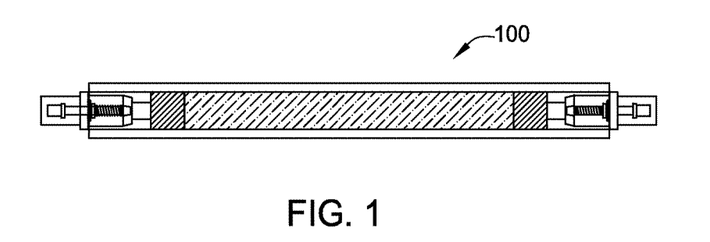
FIGS. 1, 1A, and 1B are different views of one embodiment of an isolating container assembly.
Figure 1A:
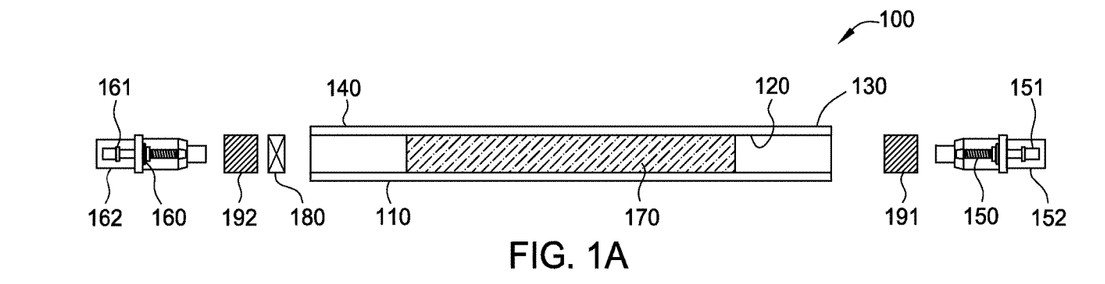
Figure 1B:
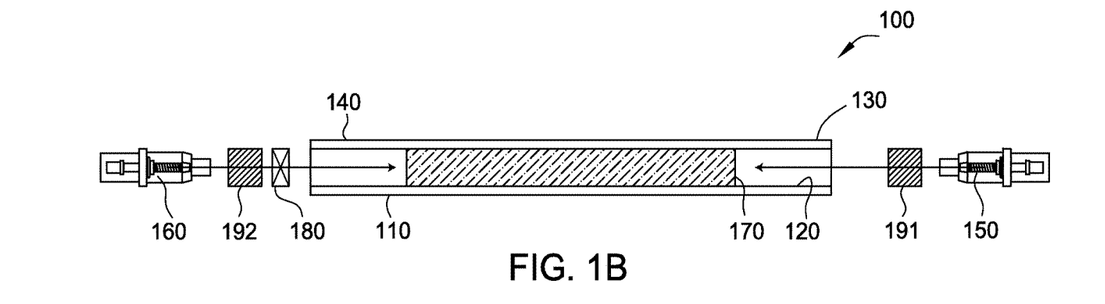

FIG. 1 illustrates one embodiment of an isolating container assembly 100 for isolating a target component from a fluid sample. FIGS. 1A and 1B show the features of the isolating container assembly 100 prior to assembly. The isolating container assembly 100 includes a body 110 having a first end 130 and a second end 140. The body 110 defines an isolating chamber 120 for retaining the isolated target component. The fluid sample may contain a desired component such as hydrocarbons and a target component such as sulfur or carbon dioxide. The target component may be a hazardous or non-hazardous material. The fluid sample may enter the sampling chamber 120, and the target component may be removed (e.g., stripped) from the fluid sample as the fluid sample passes through the sampling chamber 120. In one embodiment, the target component may be at least partially converted to a different compound and/or phase containing the target component while within the sampling chamber 120. For example, the target component may enter the sampling chamber 120 as a hazardous material and then converted to a non-hazardous or inert form while within the sampling chamber 120. Exemplary fluid samples include hydrogen sulfide ($H_2S$) containing gases, carbon monoxide (CO) containing gases, carbon dioxide ($CO_2$) containing gases, and hydrocarbon containing gases. Exemplary target components include hydrogen sulfide ($H_2S$), carbon monoxide (CO), carbon dioxide ($CO_2$), and combinations thereof. In one example, the fluid sample may be a sulfur containing natural gas sample.

The isolating container assembly 100 may be a flow through container assembly. The body 110 may be constructed of any material that does not react or does not substantially react with the fluid sample. Exemplary materials for constructing the body 110 include metal, aluminum, steel, plastic, polymer based material, carbon fiber, and combinations thereof. The body 110 may comprise an opaque, transparent, or semi-transparent material. The body 110 may be any shape configured for passage of the fluid sample. Exemplary shapes of the body 110 include a cylindrical or tubular body shape.

A first valve assembly 150 may be coupled to the first end 130 of the body and a second valve assembly 160 may be coupled to the second end 140 of the body. The first valve assembly 150 and the second valve assembly 160 may be self sealing for retaining the fluid sample within the sampling chamber 120. The first valve assembly 150 and the second valve assembly 160 may be pneumatic valve assemblies. In one embodiment, the valve assembly includes a valve stem into which a valve core is threaded, and the valve core may be a poppet valve assisted by a spring. Referring to FIG. 1A, an exemplary self-sealing valve assembly 150, 160 is a Luer activated valve, which houses one end of a spring biased valve stem 151, 161 in a tapered inner bore of a Luer female fitting 152, 162. The female fitting 152 is configured to receive a tapered male fitting to form a fluid tight connection. During connection with the female fitting, the male fitting will also depress the valve stem 151, thereby opening the valve 150 for fluid communication. An exemplary Luer activated valve is sold by Qosina Corp. Other exemplary valve assemblies include Schrader valves, Presta valves, and Dunlop valves. The first valve assembly 150 and the second valve assembly 160 may be coupled to the body 110 using any suitable attachment mechanism known in the art. Exemplary attachment mechanisms include hose barbs, vacuum tight press fit, swaging, or threads.

A reactant material 170 is positioned within the sampling chamber 120 for removing the target component from the fluid sample. The reactant material 170 may include any material suitable for interacting with the target component and "trapping" the target component via chemical or other suitable mechanisms. The reactant material 170 may trap the target component by converting the target component to a different compound and/or phase containing the target component. For example, as the fluid sample passes through the sampling chamber 120, the target component may be converted to an inert (and/or non-hazardous) form that remains in the sampling chamber 120. Typically, the reactant material 170 is selected such that the reactant material 170 does not react with or affect the desired components of the fluid sample. For example, the reactant material 170 may be selected such that the reactant material 170 does not affect either the light hydrocarbon isotope values or the ratios of one light hydrocarbon to another hydrocarbon in a natural gas sample. Optionally, the reactant material 170 is selected such that the reactant material 170 does not contain the desired component for isotopic analysis. For example, if the fluid sample is natural gas, then the initial reactant material 170 would not contain natural gas or hydrocarbons. The reactant material may be in any form sufficient to allow the desired flow of fluid throughout the sampling chamber 120. The reactant material 170 may be a solid material such as a powder or granular material. The reactant material 170 may have any suitable size. For example, the reactant material 170 may have a grain size between about 0.1 mm and about 1 mm across. In another example, the reactant material 170 may have a grain size between about 0.3 mm and about 0.5 mm across. In certain embodiments, the reactant material may be selected from zinc carbonate hydroxide ($Zn_5(CO_3)_2(OH)_6$), iron III oxide hydrate ($2FeO(OH)$), zinc acetate ($2(C_2H_3O_2)_2Zn$), iron oxide ($Fe_2O3$), and combinations thereof. The amount of reactant material 170 positioned within the sampling chamber 120 is sufficient to convert the target components in the fluid sample to a different compound and/or phase containing the target component, for example, converting the target component to a non-hazardous or inert form, without substantially restricting the flow of the fluid sample through the sampling chamber 120. In one example, the amount of reactant material 170 positioned within the sampling chamber 120 may be between 10 mg and 200 mg. In another example, the amount of reactant material 170 positioned within the sampling chamber 120 may be between 10 mg and 80 mg. In yet another embodiment, the amount of reactant material 170 positioned within the sampling chamber 120 may be between 40 mg and 50 mg.

An optional indicator material 180 may be positioned within the sampling chamber 120. The indicator material 180 may be used for indicating the presence or absence of the target component in the fluid sample. The indicator material 180 may be used to indicate that the aforementioned reactant material 170 has completely converted the target component to a non-hazardous or inert form. The indicator material 180 may undergo a visible change color to indicate the presence of the target component. As depicted in FIG. 1, if present, the indicator material 180 may be positioned downstream from the reactant material and therefore will not begin to change color until some of the target component flows past the reactant material without being converted. The indicator material 180 may comprise any material capable of indicating the presence of the target component. In certain embodiment, the indicator material 180 identifies the presence of $H_2S$ and indicates when some of the hydrogen sulfide failed to react with the reactant material. The indicator material 180 may be selected from lead acetate, copper sulfate, and combinations thereof. The indicator material 180 may be a solid material such as a powder or granular material. The indicator material 180 may have any suitable size. In one example, the indicator material 180 may have a grain size between about 1 micron and about 50 microns across. In another example, the indicator material 180 may have a grain size between about 1 micron and about 20 microns across. In yet another example, the indicator material 180 may have a grain size between about 5 microns and about 10 microns across. The indicator material 180 may be present in an amount sufficient to allow multiple reads while allowing for efficient flow of the fluid through the sampling chamber 120. In one example, the amount of indicator material 180 positioned within the sampling chamber 120 may be between 50 grams and 400 grams. In another example, the amount of indicator material 180 positioned within the sampling chamber 120 may be between 100 grams and 200 grams. In yet another example, the amount of indicator material 180 positioned within the sampling chamber 120 may be between 130 grams and 150 grams.

Optionally, a filter material 191, 192 may be positioned within the sampling chamber 120. The filter material 191, 192 may be used for holding the reactant material 170 and indicator material 180 in place without substantially interfering with the flow-though properties of the isolating container assembly 100. The filter material 191, 192 may be disposed at each end of the reactant material 170, and if used, the indicator material 180. The ability to keep the reactant material 170 and indicator material 180 compact and in place provides for uniform flow of the fluid over the reactant material 170 and the indicator material 180. The filter material 191, 192 also controls the flow of fluid by diffusing the fluid through the reactant evenly, to avoid channeling of the fluid flow through only a small portion of the reactant which could result in an inadequate conversion of the target component. The filter material 191, 192 may be a material that is inert relative to the fluids in the sampling chamber 120. Exemplary filter materials 191, 192 include polyethylene (PE) and polytetrafluoroethylene (PTFE) based materials. The filter material 191, 192 may be an inert fibrous, porous, or sintered filtering material. The pores of the filter material 191, 192 are typically smaller than the grain size of the either the reactant material 170 or the indicator material 180.

As depicted in FIG. 1, the filter materials 191, 192 are positioned on either side of the reactant material 170 to hold the reactant material 170 in place. The indicator material 180 may be disposed between the reactant material 170 and the filter material 192. It should be understood that although two filters 191, 192 are depicted in FIG. 1, any suitable number of filters may be used in the isolating container assembly 100. For example, additional filter materials may be used to isolate the reactant material 170 and/or the indicator material 180 into multiple portions.

In operation, a fluid sample enters the sampling chamber 120 via the first valve assembly 150. The fluid sample may contain a hazardous or non-hazardous target component. The fluid sample flows through the filter material 191 and contacts the reactant material 170, whereby the target component reacts with the reactant material 170. The reaction at least partially converts the target component to a different compound and/or phase containing the target component. For example, the reaction with the reactant may convert at least some of the target component from a fluid phase to a solid phase. The unreacted components of the fluid sample flows through the reactant material 170 and contacts the indicator material 180 to indicate the presence or absence of the target component in the fluid sample. In one example, when substantially all of the reactant material 170 is saturated/reacted (i.e., the reactant material has been used up via reaction with the target component) any additional target component continues to flow through the used up reactant material 170 toward the downstream indicator material 180. The additional target component contacts the indicator material 180 to generate a visible change in color, thus indicating the fluid sample leaving the reactant material 170 contains the target component and/or substantially all of the reactant material has been used up.

In one embodiment, a fluid sample containing hazardous material enters the sampling chamber 120 via the first valve assembly 150. The fluid sample flows through the filter material 191 and contacts the reactant material 170, whereby the hazardous material reacts with the reactant material 170. The reaction at least partially converts the hazardous material to a non-hazardous compound and/or different phase. For example, the reaction with the reactant material 170 may convert at least some of the hazardous material from fluid phase to a non-hazardous solid phase. The "stripped" fluid sample exits the reactant material 170 and contacts the indicator material 180 to indicate the absence of the hazardous material. Preferably, the sampling chamber 120 contains sufficient reactant material 170 to react with the target component in the fluid sample. The stripped fluid sample then flows through the filter material 192 and exits the isolating container assembly 100 via the second valve assembly 160. A sample container may be attached to second valve assembly 160 to collect the stripped fluid sample. It must be noted the stripped fluid sample may contain some amount of the target component (e.g., hazardous material) so long as the amount of the target component is within the acceptable ranges for collection, transport, or analysis.

Figure 21:
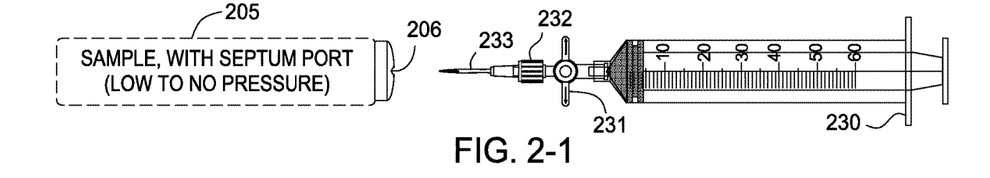

FIGS. 2-1 to 2-11 illustrate an exemplary process of isolating a target component from a fluid sample. In this exemplary process, hydrogen sulfide may be removed from a natural gas sample. In FIG. 2-1, the natural gas sample may be extracted from a source container 205 using a syringe 230. The source container 205 may include a septum port 206 for receiving the needle 233 attached to the syringe 230. The natural gas sample may be stored in the source container 205 at low or zero pressure. The syringe 230 may include a shut off valve 231 such as a quarter turn ball valve connected to a Luer male fitting 232. The needle 233 is attached to the male fitting 232.

Figure 22:
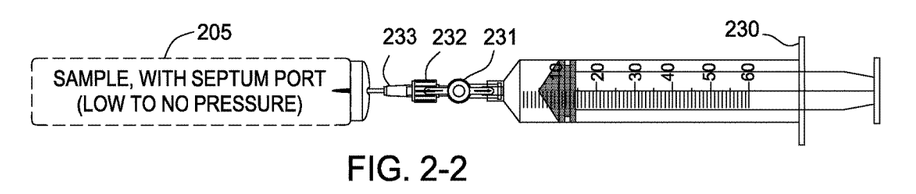

In FIG. 2-2, the needle 233 is inserted into the source container 205 to extract a first natural gas sample. The first natural gas sample may be used to purge air or other fluids from the isolating container 200. The shut off valve 231 is opened and the plunger of the syringe 230 is pulled to extract the first natural gas sample. The first natural gas sample may be extracted in an amount sufficient to purge the isolating container 200, such as between 5 ml and 100 ml, between 5 ml and 60 ml, between 5 ml and 20 ml, or any sufficient amount to purge the isolating container 200.

Figure 23:
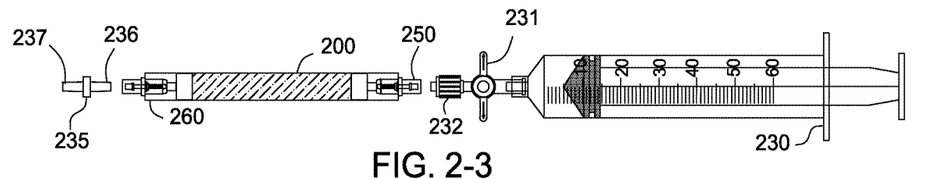

In FIG. 2-3, after extraction, the shut off valve 231 is closed and the needle 233 is removed from the syringe 230.

Figure 24:
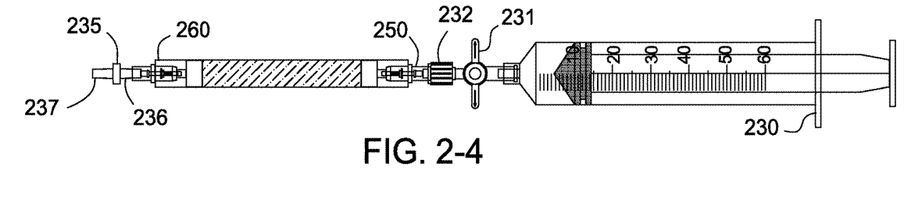

In FIG. 2-4, the syringe 230 is connected to the first self-sealing valve 250 at one end of the isolating container 200 by inserting the male fitting 232 into the female fitting of the first valve 250. During the connection, the male fitting 232 also depresses the stem of the first valve 250, thereby opening the first valve 250 for fluid communication. Also, a connector 235 is connected to the second self-sealing valve 260 at the other end of the isolating container 200. In this embodiment, the connector 235 includes a Luer male fitting 236, 237 at each end and a bore extending through the body of the connector 235. The male fitting 236 at one end is inserted into the female fitting of the second valve 260. The male fitting 236 depresses the stem of the second valve 260 thereby opening the second valve 260 for fluid communication.

Figure 25:
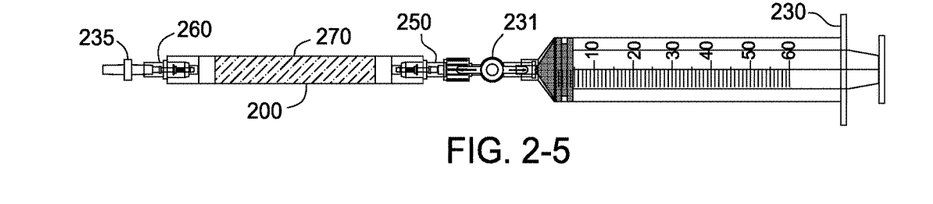

In FIG. 2-5, the shut off valve 231 is opened, and the syringe 230 is compressed to urge the first natural gas sample through the first valve 250 and the isolating container 230 to purge the isolating chamber. As the first natural gas sample passes through the reactant material 270 such as iron oxide hydrate, the hydrogen sulfide in the first natural gas sample reacts with the iron oxide hydrate and converts to a solid phase sulfur compound. The converted sulfur compound remains in the isolating chamber while the stripped natural gas sample flows through the reactant material 270 unaffected or substantially unaffected. For example, no more than 5% of the hydrocarbons in the natural gas sample are affected isotopically by the reactant material. In another example, less than 2% of the hydrocarbons are affected isotopically by the reactant material. In yet another embodiment, less than 1% of the hydrocarbons are affected isotopically by the reactant material. The stripped first natural gas sample exits the isolating container 200 via the second valve 260 and the bore of the connector 235.

Figure 26:
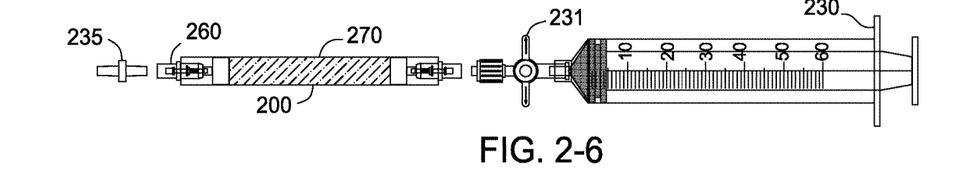

In FIG. 2-6, the connector 235 and the syringe 230 are disconnected from the isolating container 200, and the shut off valve 231 is closed. It must be noted that the purging process for the isolating container 200 described in FIGS. 2-1 to 2-6 is optional and is not required in all embodiments.

Figure 27:
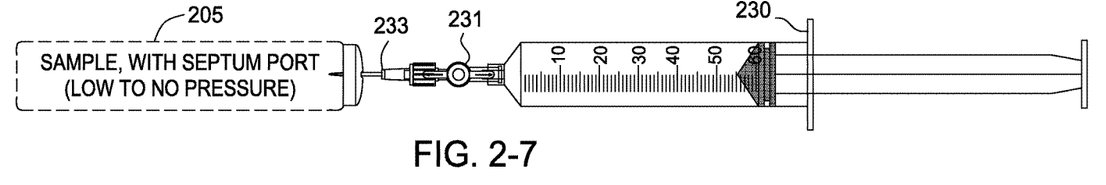

In FIG. 2-7, the needle 233 is re-attached to the syringe 230, and the needle 231 is inserted into the source container 205. Then the shut off valve 231 is opened, and the syringe 230 extracts a second natural gas sample from the source container 205. The syringe 230 may be used to extract the desired amount of natural gas sample for analysis. After extraction, the shut off valve 231 is closed.

Figure 28:
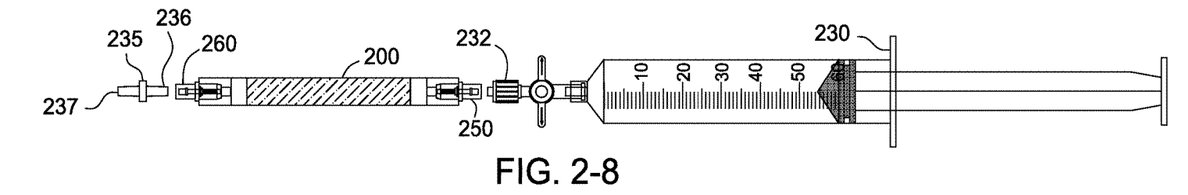

In FIG. 2-8, the needle 233 removed, and the syringe 230 is connected to the first valve 250 of the isolating container 200 by connecting the male fitting 232 to the female fitting of the first valve 250. Also, the male fitting 236 of the connector 235 is inserted into the female fitting of the second valve 260. The male fittings 232, 236 depress the respective stems and open the first valve 250 and the second valve 260 for fluid communication.

Figure 29:
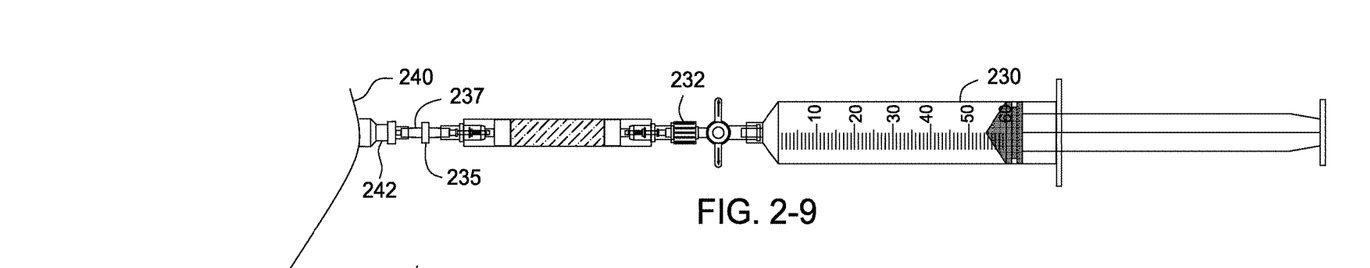

In FIG. 2-9, a sample container 240 equipped with a valve 242, such as a Luer activated valve, is attached to the connector 235. As shown, the male fitting 237 of the connector 235 is inserted into the female fitting of the valve 242. The male fitting 237 opens the valve 242 for fluid communication. Any sample container 240 suitable for holding the natural gas sample may be used. In one example, the sample container 240 is made of a material that does not change or substantially change the isotopic percentage of the hydrocarbons or the hydrocarbon ratios in the collected natural gas sample. As shown in this embodiment, the sample container 240 includes two sheets of material attached at the edges to form an internal pocket for collecting the natural gas sample. The valve 242 is attached to one of the sheets. The pocket will expand to accommodate the influx of natural gas sample.

Figure 210:
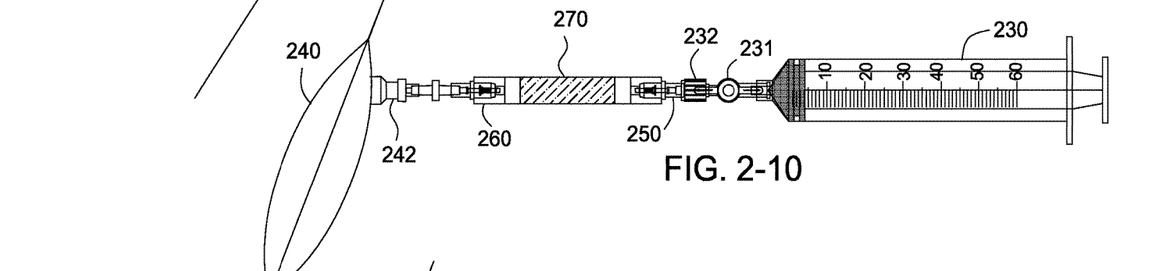

In FIG. 2-10, the shut off valve 232 is opened, and the syringe 230 is compressed to urge the second natural gas sample through the first valve 250 and the isolating container 200. As the second natural gas sample passes through the reactant material 270, the hydrogen sulfide in the natural gas sample reacts with the iron oxide hydrate and converts to a solid phase compound. The converted sulfur compound remains in the isolating chamber while the stripped natural gas sample flows through the reactant material unaffected or substantially unaffected. For example, no more than 5% of the hydrocarbons in the natural gas are affected isotopically by the reactant material. In another example, less than 2% of the hydrocarbons are affected isotopically by the reactant material. In yet another embodiment, less than 1% of the hydrocarbons are affected isotopically by the reactant material. In yet another embodiment, the effect of the reactant on the hydrocarbon ratios of the natural gas sample is less than 10%, preferably, less than 5%. The stripped second natural gas sample exits the isolating container 200 via the second valve 260 and is collected in the sample container 240.

Figure 211:
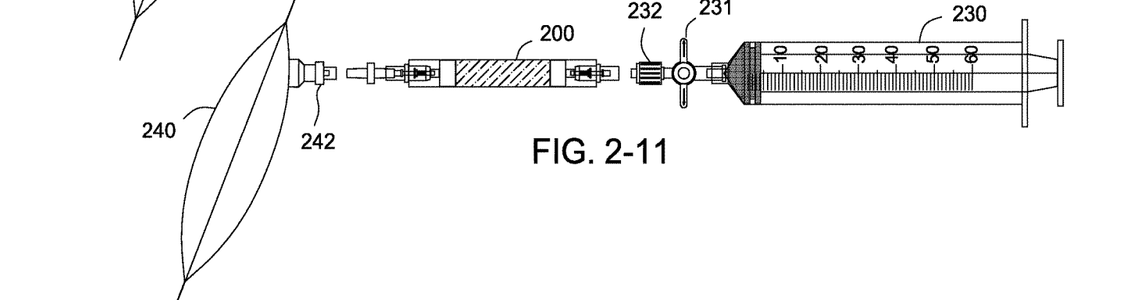

In FIG. 2-11, the sample container 240 and the syringe 230 are disconnected from the isolating container 200. Because the sulfur has been removed from the natural gas sample using the isolating container 200, the resulting sample collected in the sample container 240 can be shipped as a non-hazardous material, i.e., without being labeled as "TOXIC." After use, the isolating container 200 may be discarded without being treated as hazardous waste. If the size of the syringe 230 is inadequate to collect the desired sample amount in one extraction, multiple extractions may be performed to accumulate the desired amount of natural gas sample in the sample container 240 for analysis. For example, if the desired collected amount is 180 ml, then the process may be repeated three times using a syringe to supply three 60 ml samples into the sample container 240.

It must be noted that although the isolating container 200 is described as receiving the fluid sample from a syringe, the isolating container 200 may also be attached to any fluid source that requires the removal of a target component. For example, the isolating container 200 may be attached directly to the fluid source so that the fluid sample may be collected continuously. The fluid source may be a higher pressure source or a lower pressure. In one embodiment, a bypass line in fluid communication with a natural gas line can be used to extract a natural gas sample from the natural gas line for analysis. Before collecting the natural gas sample, the isolating container 200 may be connected to the flow path between bypass line and a sample container. In this respect, the sulfur or other targeted component may be removed prior to being collected in the sample container.

Figure 3:
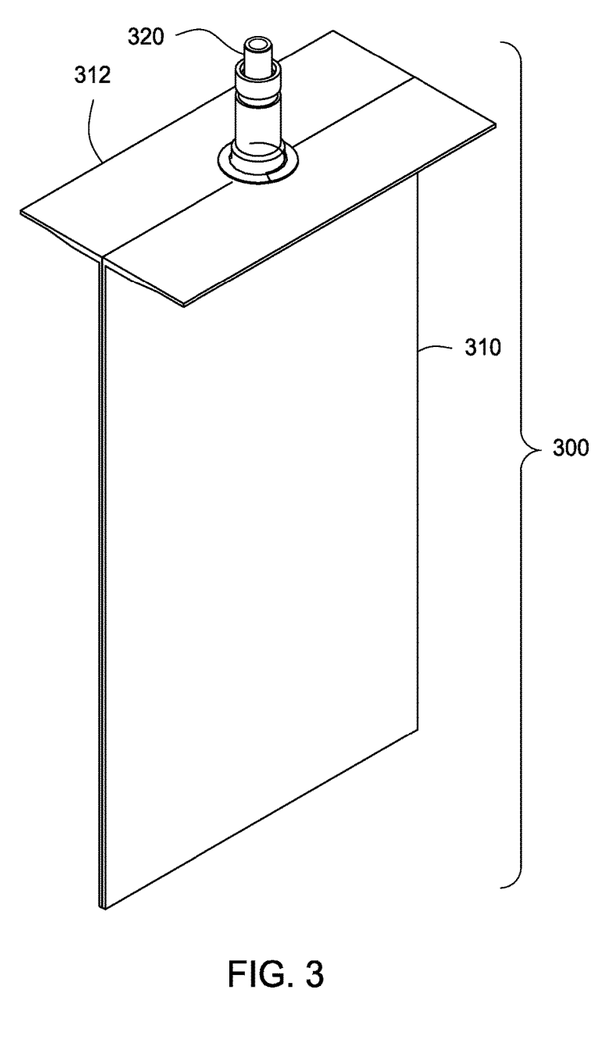
FIG. 3 illustrate an exemplary embodiment of a sample container.
Figure 3A:
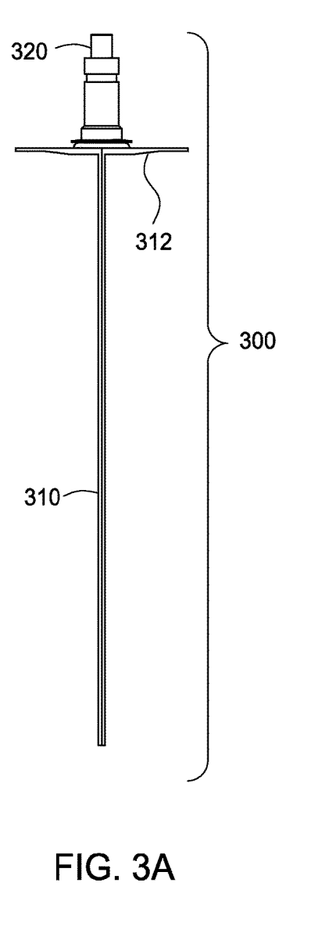
FIG. 3A is a side view of the sample container of FIG. 3.

FIG. 3 illustrate an exemplary embodiment of a sample container 300. The sample container 300 may be used as the sample container 240 shown in FIG. 2-10. FIG. 3A is a side view of the sample container 300 of FIG. 3. The sample container 300 includes a container body 310 and a flat end portion 312 and a valve assembly 320 disposed at the flat end portion 312. In one embodiment, the container body 310 includes an interior pocket and the flat end portion 312 is attached to the container body 310 such that the valve 320 fluidly communicates with the interior pocket of the container body 310. In another embodiment, the container body 310 is formed by attaching the peripheral edges of two sheets of material and the flat end portion 312 is attached to one end of the two sheets of material such that the valve 320 fluidly communicates with the interior pocket of the container body 310. As shown in FIGS. 3 and 3A, the flat end portion 312 and the container body 310 may form a T-shaped configuration. In another embodiment, the container body 310 may be in the shape of a rectangle, oval, circle, or any suitable shape for receiving a fluid sample. The container body 310 may initially have a flat configuration and later expands to increase the volume of the interior pocket to receive the fluid sample.

In one embodiment, the walls of the sample container 300 may include one or more layers of material. The container material may be selected from any suitable polymeric material such as polyethylene terephthalate ("PET"), a perfluoroplastic material such as PFA, FEP, or PTFE, a low density polyethylene ("LDPE") such as a white LDPE, an ethylene vinyl alcohol copolymer ("EVOH"), a polyamide film such as biaxially oriented nylon, and combinations thereof. In one embodiment, the container material may include multilayers of the same or different polymeric materials. For example, the container material may be made of PET, LDPE, and EVOH multi-layer material. In another embodiment, the container material may include one or more layers of metal foil or metalized film. The container material may include three, four, five, six, or more layers of materials. For example, the container material may be made of a PET layer, a metal foil layer, and an EVOH layer. In yet another embodiment, the EVOH layer is used as the innermost layer of the multi-layer container material such that the EVOH layer forms the interior surface of the pocket. The EVOH layer may have a thickness between 0.0005 inches to 0.02 inches; preferably, between 0.001 inches to 0.01 inches; more preferably, between 0.001 inches to 0.005 inches. In yet another embodiment, the PET is used as the outermost layer. In a further embodiment, at least one of the LDPE layer, foil layer, biaxially oriented nylon layer, and PTFE layer may serve as interior layers of the container material. For example, the interior layers may be a LDPE layer; a PTFE layer; a LDPE and biaxially oriented nylon bi-layer; a foil and biaxially oriented nylon bi-layer; a LDPE, foil, and biaxially oriented nylon multi-layer; a LDPE, foil, and LDPE multi-layer; a LDPE, foil, and PTFE multi-layer; and combinations thereof. In one embodiment, the container material may include a PET layer, a foil layer, and an EVOH layer. In yet another embodiment, the container material may include a metalized PET layer and an EVOH layer.

Figure 4:
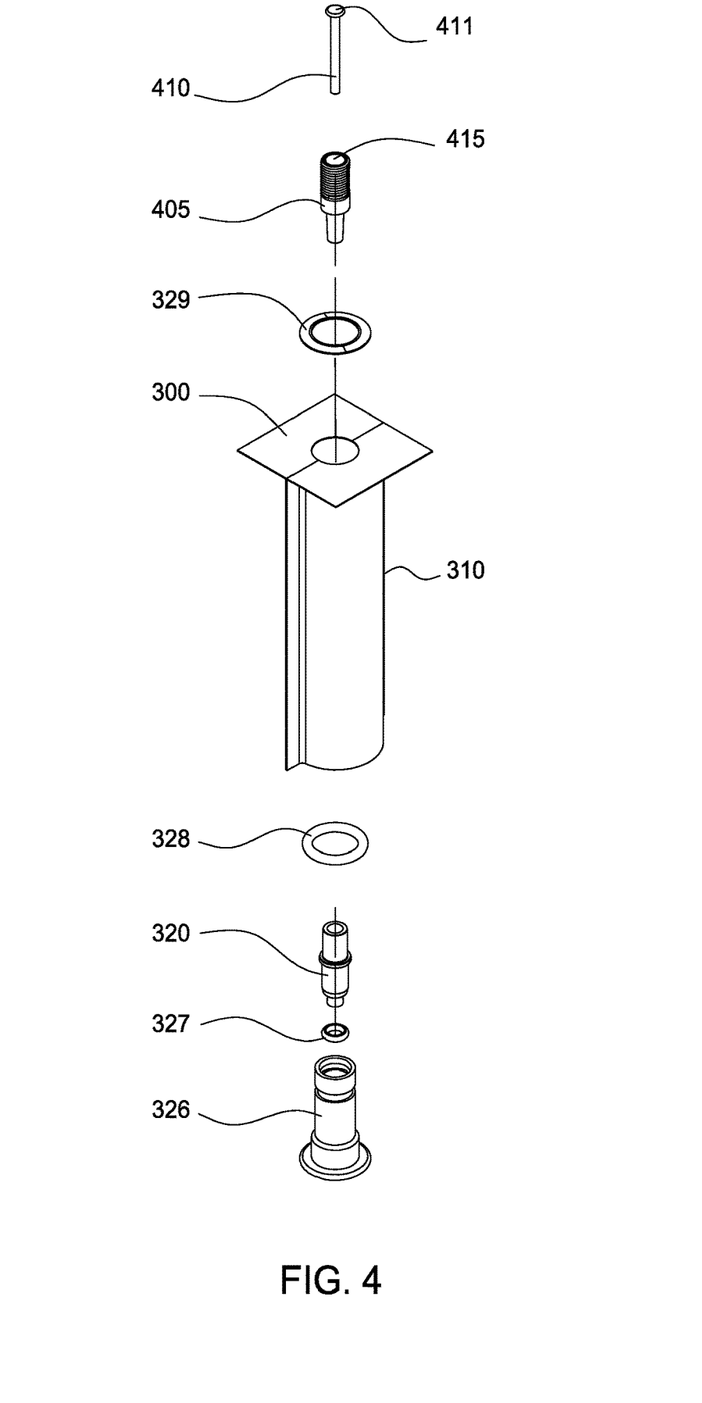
FIG. 4 shows some of the features the sample container of FIG. 3 and an embodiment of an adapter.
Figure 6A:
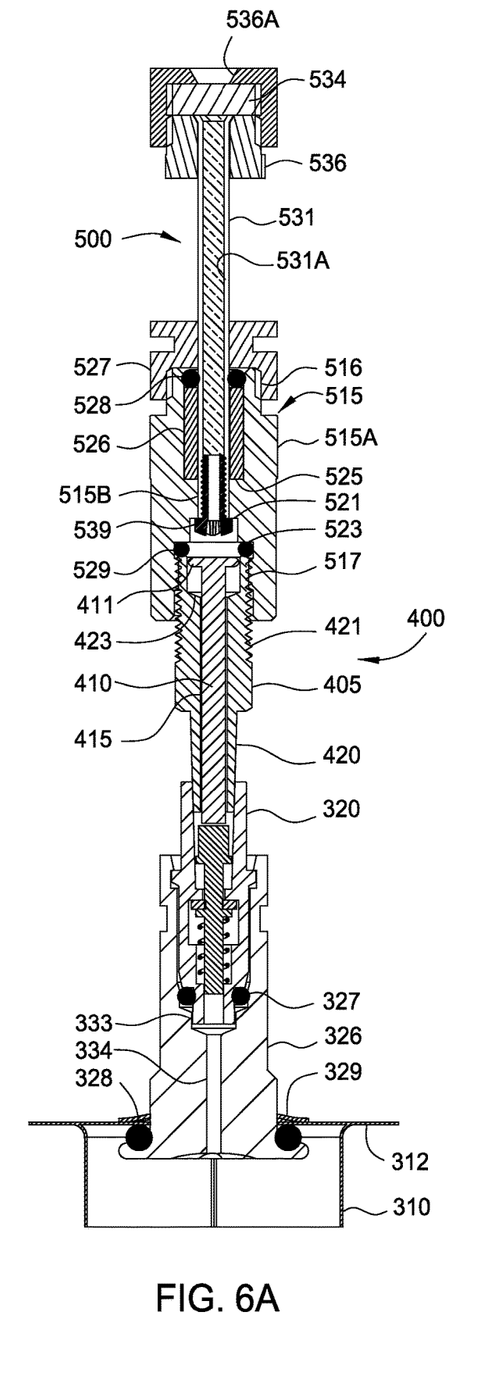
FIG. 6A is a cross-sectional view of a sample container, an adapter, and an extraction assembly assembled together and the sample container in a closed state.

The valve assembly 320 of the sample container 300 may a self-sealing valve assembly such as the valve assemblies 150, 160 described above. In one embodiment, the valve assembly 320 is a Luer activated valve. The valve assembly may be attached to the sample container 300 in any suitable manner. In one embodiment, as shown in FIG. 4, the valve assembly 320 may be attached to a valve body 326, which in turn, is attached to the sample container 300. Referring now to FIG. 6A, the valve body 326 includes a seat 333 for receiving the valve assembly 320, and a sealing member 327 such as an o-ring may be disposed between the valve body 326 and the valve assembly 320. The valve body 326 may be inserted through the flat end portion 312 of the sample container 300, and a sealing member 328 such as an o-ring may be disposed between the flat end portion 312 and the base of the valve body 326. A locking member 329 such as a speed nut may be used to retain the valve body 326 to the sample container 300.

In use, the sample container 300 may be used to collect the fluid sample leaving the isolating container 200. Referring back to FIG. 2-11, the valve assembly 320 of the T-shaped sample container 300 may be connected to the male fitting 237 of the connector 235. Upon connection, the male fitting 237 will depress the stem in the valve assembly 320, thereby opening the valve assembly 320 to receive the stripped natural gas sample leaving the isolating container 200. After collecting the natural gas sample, male fitting 237 of the connector 235 is disconnected from the valve assembly 320. The self-sealing nature of the valve assembly 320 will close the valve assembly 320 from fluid communication.

Figure 5:
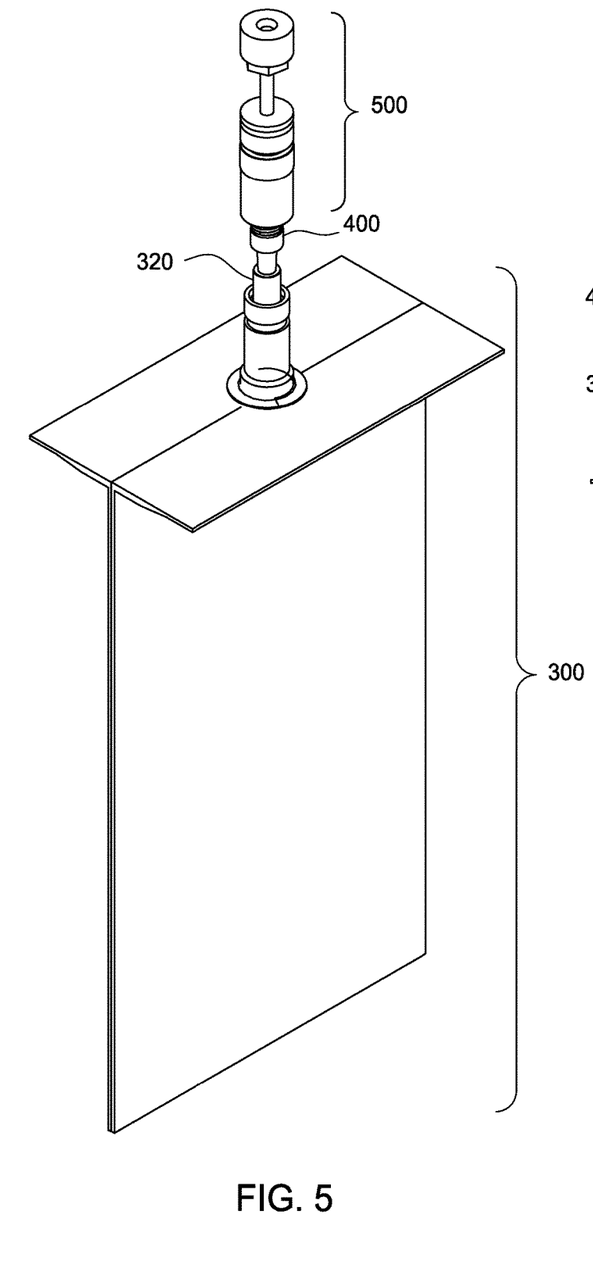
FIG. 5 is a perspective view of the sample container of FIG. 3, an embodiment of an adapter, and an extraction assembly assembled together.
Figure 5A:
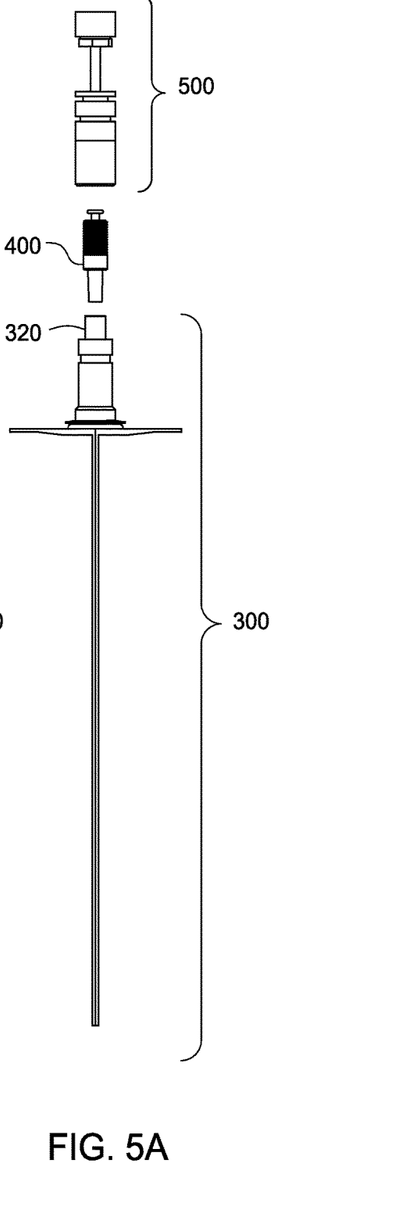
FIG. 5A shows the sample container, the adapter, and the extraction assembly before assembly.

In another embodiment, the fluid sample in the sample container 300 may be removed for analysis. For example, the sample container 300 may be coupled to an extraction assembly to remove the fluid sample for analysis. An exemplary extraction assembly is disclosed in U.S. Patent Application Publication No. 2008/0282814, which is incorporated herein by reference in its entirety, including the description related to the extraction assembly 14. In one embodiment, an adapter 400 may be used to couple the extraction assembly 500 to the valve assembly 320 of the sample container 300, as shown in FIGS. 5 and 5A. FIG. 5 is a perspective view of the sample container 300, the adapter 400, and the extraction assembly 500 assembled together. FIG. 5A shows the sample container 300, the adapter 400, and the extraction assembly 500 before assembly.

Figure 7:
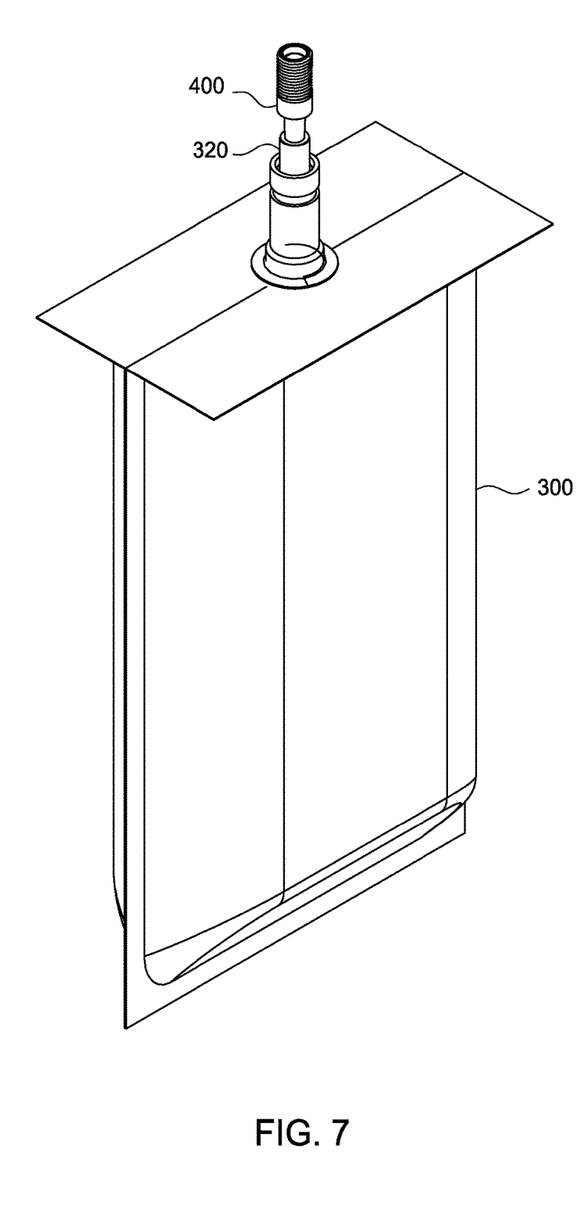
FIG. 7 shows an adapter coupled to the valve of one embodiment of a sample container.
Figure 8:
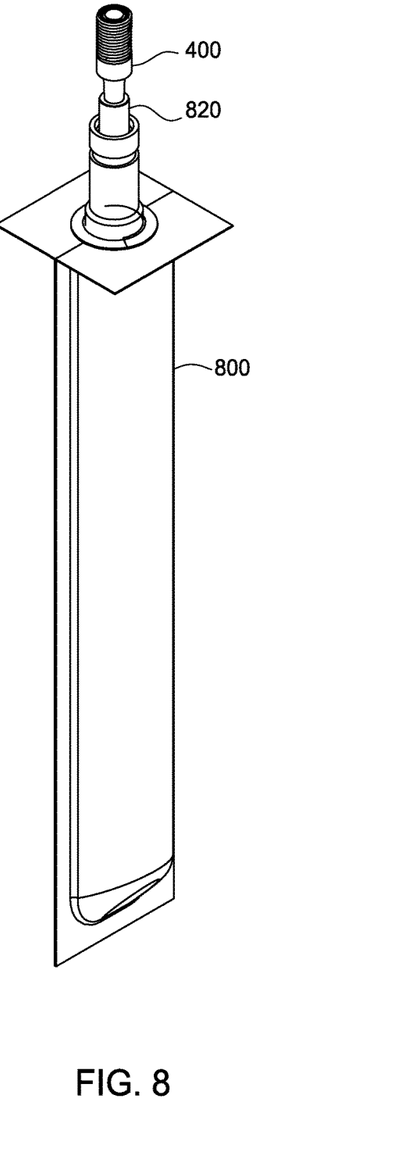
FIG. 8 shows an adapter coupled to the valve of another embodiment of a sample container.

Referring now to FIGS. 4 and 6A, the adapter 400 includes a connect body 405 and a pin 410 disposed in a bore 415 of the connect body 405. The pin 410 optionally includes a larger diameter head 411 disposed at an upper end of the pin 410. The bore 415 may include a larger diameter section to accommodate the head 411 of the pin 410. The bottom of the larger diameter section forms a shoulder 423 in the bore 415. The adapter 400 may connect to the extraction assembly 500 using any suitable connection mechanism. For example, threads 421 may be provided on the outer surface of the upper portion of the connect body 405 for connection with the extraction assembly 500. The lower portion of the adapter 400 includes a Luer male fitting 420 for connection with the female fitting of the valve assembly 320 of the sample container 300. FIG. 6A shows the valve assembly 320 of the sample container 300 in the closed position and the adapter 400 connected to the valve assembly 320. As shown in FIG. 6A, the pin 410 has a sufficient length such that the bottom of the pin 410 rests on the stem of the valve assembly 320, and a gap exists between the head 411 of the pin 410 and the shoulder 423 in the bore 415. In additional, it can be seen that the end of the male fitting 320 does not depress the stem of the valve 320. FIG. 7 shows an adapter 400 coupled to the valve 320 of the sample container 300. FIG. 8 shows an adapter 400 coupled to the valve 820 of another embodiment of a sample container 800.

FIG. 6A also illustrates an exemplary embodiment of an extraction assembly 500. The extraction assembly 500 includes a coupler 515 having a coupler body 515A. The coupler body 515A has a central longitudinal bore 515B which allows for fluid flow. The coupler 515 also has an externally threaded first body end 516 and an internally threaded second body end 517. The central longitudinal bore 515B is divided into segments of varying diameters, thereby creating a first shoulder 521, a second shoulder 523, and a third shoulder 525. A first sealing member 529 such as a rubber o-ring rests against the second shoulder 523. The first sealing member 529 creates a seal when the internally threaded second body end 517 is connected to the external threads 421 of the adapter 400. An annular bushing 526 is disposed on the third shoulder 525, and a second sealing member 528 such as an o-ring is disposed on the annular bushing 526. An internally threaded bushing retaining cap 527 having a central bore, is disposed over the externally threaded first body end 516. A stem 531 is axially movable and partially disposed within the central bore of bushing retaining cap 527, the annular bushing 526, and the bore 515B of the coupler body 515A. The second sealing member 528 prevents the passage of fluid around the stem 531. Stem 531 includes a central bore 531A and a head portion 539 having a larger diameter than the stem 531 and thereby is able to rest on the first shoulder 521 and to secure the stem 531 within the coupler body 515A. The head portion 539 includes a bore that communicates with the central bore 531A of the stem 531. A retaining member 536 is attached to the upper end of the stem 531. The retaining member 536 may include a septum seat and a septum cap. A septum 534, which may be composed of a penetrable material such as rubber, is disposed on the septum seat. The septum 534 may be accessed through an aperture 536A in the retaining member 536. An optional spring may be disposed between the retaining member 536 and the bushing retaining cap 527.

Figure 6B:
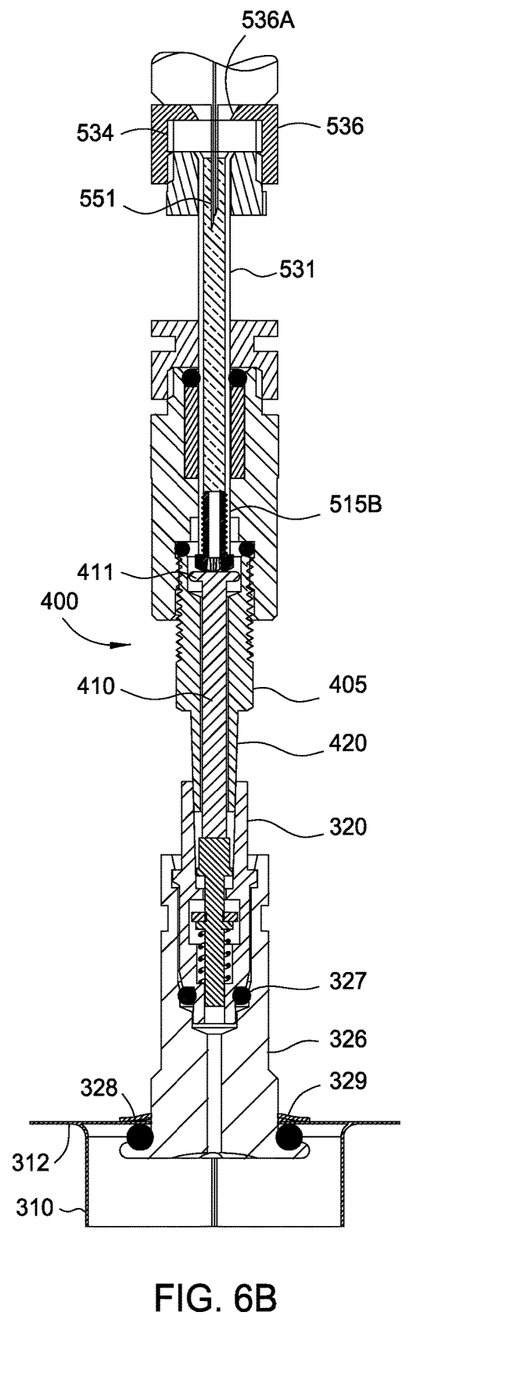
FIG. 6B shows the sample container of FIG. 6A in an open state.

Prior to extracting the fluid sample from the sample container 300, the extraction assembly 500 is threadedly attached to the adapter 400, and the Luer male fitting 420 of the adapter 400 is inserted into the female fitting of the valve assembly 320 of the sample container, as shown in FIG. 6A. In FIG. 6A, the valve assembly 320 is in the closed position. To extract the fluid sample, a needle 551, such as a hypodermic needle, is inserted through the aperture 536A of the retaining member 536. Depressing the retaining member 536 causes the stem 531 to push the pin 410 down against the stem of the valve assembly 320. As a result, as shown in FIG. 6B, the valve assembly 320 is opened for fluid communication with the pocket of the sample container 300, thereby allowing the sample fluid to be extracted from the sample container 300. The sample fluid may flow from the sample container 300, through the valve 320, through the bore 415 of the adapter 400, through the bore 515B, and into the needle 551. After withdrawal, pressure on the retaining member 536 is relieved, thereby closing the valve assembly 320.

The embodiments described herein provide several advantages over prior methods of collecting hazardous fluid samples. In certain embodiments, a fluid sample may be flowed through an isolating container to remove a target component such as a hazardous material from the fluid sample before being collected in a sample container. After collection in the sample container, the scrubbed fluid sample may be transported without additional hazardous material restraints.

In certain embodiments, the sample container may include a T-shaped configuration, wherein the valve assembly is disposed in a flat end portion of the sample container. Without wising to be bound by theory, it is believed that positioning the valve assembly at the flat end portion instead of a wall of the sample container reduces the stress on the wall of the sample container and also facilitates attachment to other devices such as the extraction assembly. In one embodiment, the sample container may be made from a material that does not substantially affect its contents. For example, the sample container material may be selected to minimize the absorptive effect on its contents.

In one embodiment, an isolating container for removing a component from a fluid sample includes a body defining a sampling chamber having a first end and a second end; a first valve assembly coupled to the first end; a reactant material positioned within the sampling chamber for reacting with the component; and a second valve assembly coupled to the second end, wherein the fluid sample enters the sampling chamber through the first valve assembly and exits through the second valve assembly.

In another embodiment, a method for collecting a fluid sample includes flowing the fluid sample into an isolating container, wherein the isolating container includes a reactant material; removing a component from the fluid sample by reacting the component with the reactant material; and collecting the fluid sample leaving the isolating container into a sample container.

In another embodiment, a sample container for collecting a fluid sample includes a container body; a flat end portion; and a valve assembly disposed at the flat end portion for accessing the interior of the container body.

In another embodiment, an adapter for coupling a Luer activated valve to an activating device includes a connect body having a bore, a first end for coupling with the Luer activated valve, and a second end for coupling with the activating device; and a pin movably disposed in the bore of the connect body, wherein the pin is movable by the activating device to activate the Luer activated valve.

In another embodiment, a fluid sample collection assembly includes a sample container coupled to an isolating container for selective fluid communication with a second valve assembly of the isolating container. The isolating container includes a body defining a sampling chamber having a first end and a second end; a first valve assembly coupled to the first end; a reactant material positioned within the sampling chamber for reacting with the component; and a second valve assembly coupled to the second end, wherein the fluid sample enters the sampling chamber through the first valve assembly and exits through the second valve assembly. The sample container includes a container body; a flat end portion; and a valve assembly disposed at the flat end portion for accessing the interior of the container body.

In another embodiment, a fluid sample extraction assembly includes a sample container coupled to an extraction apparatus, wherein the extraction apparatus is configured to open the sample container. The sample container includes a container body; a flat end portion; and a valve assembly disposed at the flat end portion for accessing the interior of the container body. The extraction apparatus includes a coupler body having a bore therethrough; and a stem movable disposed in the bore, wherein the stem is configured to open the valve assembly for extracting a fluid sample from the sample container. In one embodiment, the extraction assembly may include an adapter for coupling the extraction assembly to the sample container. The adapter includes a connect body having a bore, a first end for coupling with the valve assembly using a Luer fitting; and a pin movably disposed in the bore of the connect body, wherein the pin is movable by the extraction apparatus to activate the valve assembly.

In one or more of the embodiments described herein, at least one of the first valve assembly and the second valve assembly is a self-closing valve assembly.

In one or more of the embodiments described herein, at least one of the first valve assembly and the second valve assembly comprises a Luer activated valve.

In one or more of the embodiments described herein, the reactant material converts the component to an inert form.

In one or more of the embodiments described herein, the reactant material converts the component to a non-hazardous form.

In one or more of the embodiments described herein, the reactant material is selected from the group consisting of: zinc carbonate hydroxide ($Zn_5(CO_3)_2(OH)_6$), iron III oxide hydrate ($2FeO(OH)$), zinc acetate ($2(C_2H_3O_2)_2Zn$), iron oxide ($Fe_2O3$), and combinations thereof.

In one or more of the embodiments described herein, a filtering material positioned within the sampling chamber.

In one or more of the embodiments described herein, the filtering material is selected from the group consisting of: polyethylene (PE) and polytetrafluoroethylene (PTFE) based materials.

In one or more of the embodiments described herein, the component removed is hydrogen sulfide ($H_2S$) and the reactant material converts hydrogen sulfide ($H_2S$) to an inert form.

In one or more of the embodiments described herein, the reactant material does not substantially affect the isotopes in the fluid sample.

In one or more of the embodiments described herein, the method includes purging the isolating container prior to collecting the fluid sample in the sample container.

In one or more of the embodiments described herein, the fluid sample is natural gas and the component is hydrogen sulfide.

In one or more of the embodiments described herein, the container body and the flat end portion forms a T-shaped configuration.

In one or more of the embodiments described herein, the valve assembly is a self-sealing valve assembly.

In one or more of the embodiments described herein, the valve assembly comprises a Luer activated valve.

In one or more of the embodiments described herein, the sample container comprises one or more layers of elastomeric material.

In one or more of the embodiments described herein, one or more layers of the sample container is selected from the group consisting of polyethylene terephthalate ("PET"), a perfluoroplastic material, a low density polyethylene ("LDPE"), an ethylene vinyl alcohol copolymer ("EVOH"), a polyamide film such as biaxially oriented nylon, and combinations thereof.

In one or more of the embodiments described herein, the sample container comprises multiple layers of the same or different polymeric materials.

In one or more of the embodiments described herein, the sample container further comprises at least one of a metal foil layer and a metalized film.

In one or more of the embodiments described herein, the sample container includes an EVOH layer.

In one or more of the embodiments described herein, the sample container includes a PET layer.

In one or more of the embodiments described herein, the pin includes a head portion having a larger diameter, wherein the head portion is disposed in a larger diameter segment of the bore.

In one or more of the embodiments described herein, the adapter includes threads for coupling with the activating device.

In one or more of the embodiments described herein, the activating device comprises an extraction assembly.

In one or more of the embodiments described herein, the fluid sample collection assembly includes a connector having a Luer male fitting at each end, wherein the connector is coupled to the second valve assembly and the valve assembly of the sample container.

In one or more of the embodiments described herein, the extraction assembly includes an adapter for coupling the extraction assembly to the sample container.

In one or more of the embodiments described herein, the adapter includes a connect body having a bore, a first end for coupling with the valve assembly using a Luer fitting; and a pin movably disposed in the bore of the connect body, wherein the pin is movable by the extraction apparatus to activate the valve assembly.

While the foregoing is directed to embodiments of the present invention, other and further embodiments of the invention may be devised without departing from the basic scope thereof, and the scope thereof is determined by the claims that follow.

The invention claimed is:

1. A sampling assembly, comprising:
   an isolating container for removing a component from a fluid sample containing hydrocarbons, comprising:
   a body defining a sampling chamber having a first end and a second end;
   a first valve assembly coupled to the first end;
   a reactant material positioned within the sampling chamber for reacting with the component, wherein the reactant material is substantially unreactive with hydrocarbons in the fluid sample; and
   a second valve assembly coupled to the second end, wherein the hydrocarbons of the fluid sample enters the sampling chamber through the first valve assembly and exits through the second valve assembly, wherein the hydrocarbons of the fluid sample exiting through the second valve assembly is collected for isotopic analysis;
   a syringe for supplying the fluid sample to the first end of the isolating containing container; and
   a sample container connected to the second end for collecting the hydrocarbons of the fluid sample exiting the second end.

2. The isolating container of claim 1, wherein at least one of the first valve assembly and the second valve assembly is a self-closing valve assembly.

3. The isolating container of claim 2, wherein at least one of the first valve assembly and the second valve assembly comprises a Luer activated valve.

4. The isolating container of claim 1, further comprising a filtering material positioned within the sampling chamber.

5. The isolating container of claim 4, wherein the filtering material is selected from the group consisting of: polyethylene (PE) and polytetrafluoroethylene (PTFE) based materials.

6. The isolating container of claim 1, wherein the component is hydrogen sulfide ($H_2S$) and the reactant material converts hydrogen sulfide ($H_2S$) to an inert form.

7. The isolating container of claim 1, wherein less than 5% of the hydrocarbons in the fluid sample are affected isotopically by the reactant material.

8. The isolating container of claim 1, wherein less than 2% of the hydrocarbons in the fluid sample are affected isotopically by the reactant material.

9. The isolating container of claim 8, wherein the reactant material is iron III oxide hydrate (2FeO(OH)).

10. The isolating container of claim 9, wherein the fluid sample comprises natural gas.

11. The isolating container of claim 1, wherein less than 1% of the hydrocarbons in the fluid sample are affected isotopically by the reactant material.

12. The isolating container of claim 1, wherein an effect of the reactant material on a hydrocarbon ratio of the fluid sample is less than 5%.

13. The isolating container of claim 1, wherein the reactant material is iron III oxide hydrate (2FeO(OH)).

14. The sampling assembly of claim 1, wherein the reactant material converts the component to an inert form.

15. The sampling assembly of claim 14, wherein the reactant material is selected from the group consisting of: zinc carbonate hydroxide ($Zn_5(CO_3)_2(OH)_6$), iron III oxide hydrate (2FeO(OH)), zinc acetate ($2(C_2H_3O_2)_2Zn$), iron oxide ($Fe_2O3$), and combinations thereof.

* * * * *